(12) United States Patent
Thilwind et al.

(10) Patent No.: US 8,353,865 B2
(45) Date of Patent: Jan. 15, 2013

(54) BREAST PUMP SYSTEM

(75) Inventors: Rachel Estelle Thilwind, Eindhoven (NL); Marjolein Irene Van Lieshout, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/121,204

(22) PCT Filed: Sep. 28, 2009

(86) PCT No.: PCT/IB2009/054235
§ 371 (c)(1),
(2), (4) Date: Mar. 28, 2011

(87) PCT Pub. No.: WO2010/038184
PCT Pub. Date: Apr. 8, 2010

(65) Prior Publication Data
US 2011/0190695 A1 Aug. 4, 2011

(30) Foreign Application Priority Data
Oct. 3, 2008 (EP) ...................................... 08165801

(51) Int. Cl.
*A61M 1/06* (2006.01)
(52) U.S. Cl. ........................................................ 604/74

(58) Field of Classification Search ..................... 604/73, 604/74
See application file for complete search history.

(56) References Cited

U.S. PATENT DOCUMENTS

| | | | |
|---|---|---|---|
| 5,885,246 A * | 3/1999 | Ford ............................... 604/74 |
| 7,166,087 B2 * | 1/2007 | Silver et al. ..................... 604/74 |
| 7,468,043 B2 * | 12/2008 | Morton et al. ................. 600/573 |
| 7,682,334 B2 * | 3/2010 | Greter et al. .................... 604/74 |
| 2001/0031911 A1 * | 10/2001 | Khouri ............................ 600/38 |
| 2002/0198489 A1 | 12/2002 | Silver et al. |
| 2004/0029486 A1 * | 2/2004 | Greter et al. .................... 450/39 |
| 2010/0130921 A1 * | 5/2010 | Kobayashi et al. ............. 604/74 |
| 2012/0083731 A1 * | 4/2012 | Gottenbos et al. ............. 604/75 |

FOREIGN PATENT DOCUMENTS

| | | |
|---|---|---|
| EP | 0310326 | 4/1989 |
| EP | 1184044 | 3/2002 |
| WO | 2006065884 | 6/2006 |

* cited by examiner

*Primary Examiner* — Nicholas Lucchesi
*Assistant Examiner* — Aarti B Berdichevsky

(57) ABSTRACT

A breast receiving funnel (5) for a breast pump (1) comprising an expandable layer (18) formed from a hydrogel which is configured to expand such that an inner surface of the breast receiving funnel (5), against which a user's breast is locatable, swells towards said user's breast to apply a positive pressure thereto and aid the expression of milk therefrom.

15 Claims, 3 Drawing Sheets

BREAST PUMP SYSTEM

FIELD OF THE INVENTION

The present invention relates to a breast-receiving funnel for a breast pump operable to extract milk from a user. The present invention also relates to a breast pump comprising a breast-receiving funnel and an insert adapted to fit on a breast receiving funnel.

BACKGROUND OF THE INVENTION

Breast pumps are well known devices for extracting milk from a breast of a user. A breast pump may be used if the baby is not itself able to extract the milk, or if the mother is separated from the baby, for example if away from the baby at work. The use of a breast pump to extract milk may also be used to stimulate lactation in women with a low milk supply.

Conventional breast pumps make use of a vacuum to induce milk extraction from a nursing mother's breast. The pumping action of the device draws the milk from the nipple, to a collection vessel, and may be adjusted to the preferences of the lactating female.

Breast pumps may be manually operated, for example by squeezing a handle or operation of a foot pedal. Breast pumps may also be electrically driven by a small electric motor.

A problem with conventional breast pumps is that users are known to suffer from discomfort or difficulty when using such a conventional breast pump. Female breasts vary in size and shape, however conventional breast pumps are manufactured to a uniform size which do not account for this. Therefore, there is the difficulty of maintaining contact and attachment.

When an infant feeds from its mother's breast, the baby applies two actions to obtain milk, sucking and a peristaltic movement created by the action of the infant's tongue on the nipple and areola of the mother's breast. The sucking action applies a negative pressure to latch onto the breast and induce milk flow. The infant can also perform a peristaltic stripping motion over the areola and nipple to induce milk flow from the breast. In this motion a rhythmic contraction and expansion motion is performed to induce the milk flow.

Furthermore, conventional breast pumps do not help to prevent or relieve engorgement. Currently, a user needs to steer her baby to feed with the chin against the engorged region of the breast, but this is inconvenient with the positioning of the baby. Conventional breast pumps do not address the problem of preventing or relieving engorgement.

Therefore, it is an object of the invention to provide a breast pump which substantially alleviates or overcomes the problems mentioned above and aids the expression of breast milk from a breast in a way that is more analogous to the suckling infant.

Accordingly, the present invention provides a breast receiving funnel for a breast pump comprising an expandable layer formed from a hydrogel which is configured to expand such that an inner surface of the breast receiving funnel, against which a user's breast is locatable, swells towards said user's breast to apply a positive pressure thereto and aid the expression of milk therefrom.

Preferably, the inner surface of the breast receiving funnel is configured to contact a nipple and/or areola of the user's breast.

SUMMARY OF THE INVENTION

The breast receiving funnel may further comprise an activating element which is operable to cause the expandable layer to expand or contract.

Advantageously, the activating element is disposed in the expandable layer.

Preferably, the activating element is operable to emit heat and/or light energy and the expandable layer is activated by said heat and/or light energy such that it expands or contracts.

Conveniently, the activating element is an LED.

The breast receiving funnel may further comprise a plurality of activating elements.

In one embodiment, a surface of the expandable layer forms the inner surface of the breast receiving funnel.

In another embodiment, a protective membrane is disposed on a surface of the expandable layer and the protective membrane forms the inner surface of the breast receiving funnel.

Advantageously, the protective membrane is resilient.

Conveniently, the breast-receiving funnel further comprises a rigid shell and the expandable layer is disposed between the rigid shell and the protective membrane.

Preferably, the protective membrane seals to said rigid shell such that the expandable layer is enclosed therein.

The breast receiving funnel for a breast pump may further comprise a control unit configured to operate the activating elements in a sequential manner such that zones of the inner surface, associated with each activating element, swell periodically in a predetermined sequence causing the zones of the inner surface to move inwardly and outwardly relative to the user's breast and apply a peristaltic pressure thereto.

In a preferred embodiment, the breast receiving funnel is conical and the control unit is configured to operate activating elements disposed in an arcuate region of the expandable layer such that only zones of the inner surface associated with activating elements in said arcuate portion swell towards said user's breast.

Advantageously, the inner surface of the breast receiving funnel converges from an opening for receiving a user's breast to an inner end of the breast receiving portion, and the density of the number of activating elements increases towards the inner end.

Preferably, the expandable layer comprises a plurality of discrete cells of hydrogel which are independently activatable such that a zone of the inner surface associated with each discrete cell is configured to swell independently to an adjacent zone and an activating element may be associated with each discrete cell.

According to another aspect of the present invention, there is also provided a breast pump comprising a breast-receiving funnel.

The breast pump may further include means for generating a negative pressure in the funnel when a user's breast is received therein.

Preferably, the means for generating a negative pressure comprises a vacuum pump disposed in a main body of the breast pump.

According to yet another aspect of the present invention, there is also provided an insert adapted to fit on a breast-receiving funnel of a breast pump comprising an expandable layer formed from a hydrogel which is configured to expand such that an inner surface of the insert, against which a user's breast is locatable, swells towards said user's breast to aid the expression of milk therefrom.

Conveniently, a protective membrane is disposed on a surface of the expandable layer and the protective membrane forms the inner surface of the insert.

Preferably, the protective membrane encloses the expandable layer such that the expandable layer is sealed therein.

Advantageously, the insert further comprises a rigid shell and the expandable layer is disposed between the rigid shell and the protective membrane.

The protective membrane may seal to said rigid shell such that the expandable layer is enclosed therein.

According to another aspect of the present invention, there is also provided a method of inducing the expression of milk from a user's breast using a breast receiving funnel for a breast pump comprising an expandable layer formed from a hydrogel, the method including the steps of locating a user's breast against an inner surface of the breast receiving funnel and activating the expandable layer such that the inner surface of the breast receiving funnel swells to apply a positive pressure to the user's breast and aid the expression of milk therefrom.

Preferred embodiments of the invention will now be described, by way of example only, with reference to the accompanying drawings, in which:

BRIEF DESCRIPTION OF THE EMBODIMENTS

Figure 1:
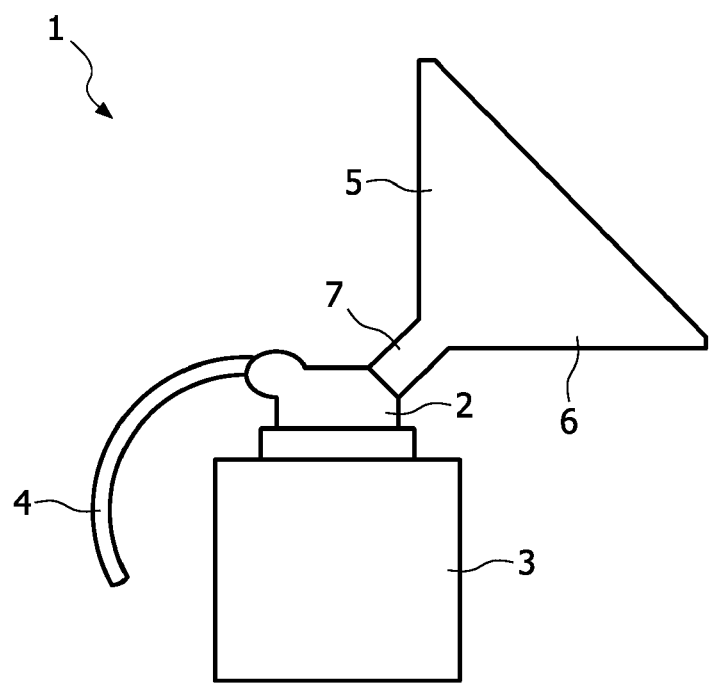
FIG. 1 illustrates a side view of a breast pump according to an the present invention.

Referring now to the drawings, FIG. 1 illustrates an embodiment of a breast pump 1 for extracting milk from a user according to the present invention. The breast pump unit 1 comprises a main body 2 and a milk-receiving vessel 3. The milk receiving vessel 3, which may take the form of a feeding bottle for an infant or baby, is attached to the main body 2 by a screw fitting (not shown), although it will be understood that alternative releasable attachment means may be used, such as clips (not shown). A seal (not shown) is disposed between the main body 2 and milk receiving vessel 3.

A vacuum pump unit (not shown) is formed in the main body 2, to create a vacuum, as will be described hereinafter and a handle 4 extends from the main body 2. The handle 4 is manually operable to operate the vacuum pump unit (not shown). The vacuum pump unit (not shown) is conventional and so no further description of the pump unit will be given here. Alternatively, the vacuum pump unit (not shown) may be motorized. In this case, the handle 4 is not present and the motorized vacuum pump unit (not shown) is powered by batteries disposed in the main body 2.

Figure 2:
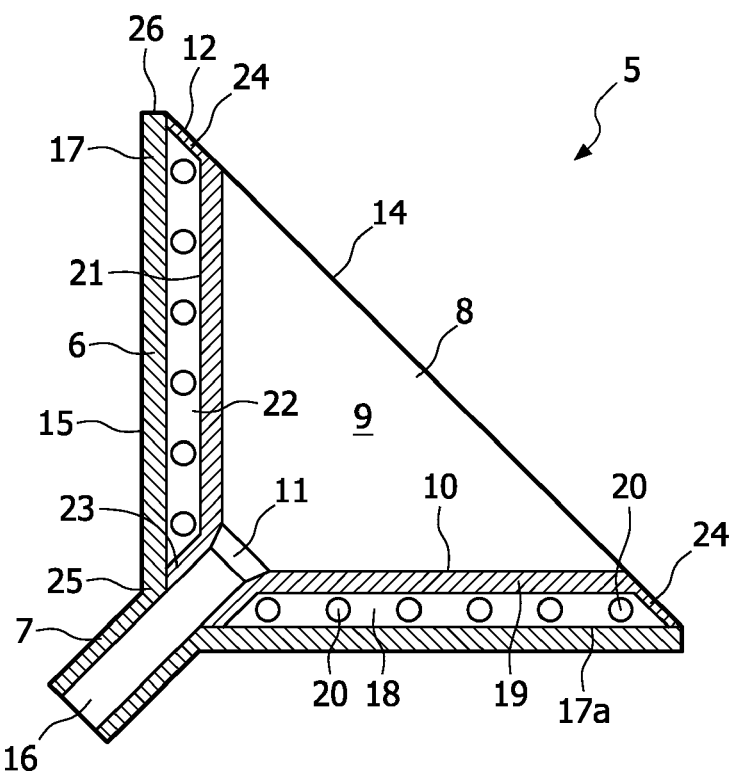
FIG. 2 illustrates a cross sectional view of a breast receiving funnel of the breast pump as shown in FIG. 1 according to a first embodiment of the present invention.

A breast receiving funnel 5 is fixedly attached to the main body 2 for receiving the breast of a user. Referring to FIG. 2, a funnel 5 according to a first embodiment of the present invention is shown. The funnel 5 comprises a conical portion 6 and a cylindrical portion 7. The conical portion 6 is open at an upper end 8 and converges towards the cylindrical portion 7. A hollow recess 9 is formed therein from the upper end 8.

An inner surface 10 of the hollow recess 9 converges from the upper end 8 to a lower end 11. The conical portion 6 further comprises a circumferentially extending upper face 12 at the upper end 8 which extends around an opening 14 to the hollow recess 9 and a funnel outer surface 15.

Although in the present embodiment the funnel 5 is fixedly mounted to the main body 2 of the breast pump 1 it will be understood that the invention is not limited thereto. The funnel 5 may be removable mounted to the main body 2 of the breast pump 1 to aid cleaning or sterilization of the funnel 5 and main body 1. Additionally, such a funnel 5 is mountable to an existing breast pump such that the funnel 5 is retrofitted to an existing breast pump.

The cylindrical portion 7 of the funnel 5 comprises a hollow passage 16 which communicates the main body 2 with the hollow recess 9 at the lower end 11 such that a fluid passageway is provided between the hollow recess 9 of the funnel 5 and the milk receiving vessel 3. The hollow passage 16 also provides a passageway to enable the vacuum pump unit (not shown) disposed in the main body 2 to create a negative pressure in the hollow recess 9 of the funnel 5 when a user's breast is disposed therein.

The conical portion 6 of the funnel 5 comprises an outer shell 17, an expandable layer 18 and impermeable protective membrane 19.

In this embodiment the outer shell 17 is integrally formed with the cylindrical portion 7, and the outer shell 17 and cylindrical portion 7 are formed from a stiff material, for example a plastic. Together the outer shell 17 and cylindrical portion 7 define the overall shape of the funnel 5.

The expandable layer 18 is disposed on an inner face 17a of the outer shell 17 and extends there around, between the lower and upper ends 11,12 of the funnel 5, such that the expandable layer 18 extends over the inner face 17a of the outer shell 17. In this embodiment the expandable layer 18 is formed from a hydrogel or polymer gel. Said hydrogels or polymer gels expand or contract dependent on environmental conditions. In this embodiment, hydrogels are used which respond to heat light and/or heat and so are activated and expand when light or heat energy is applied to them. The heat energy emitted also provides a more comfortable experience for a user. It will be understood that hydrogels may be used which are actuated in response to alternative stimulations, such as an electrical current.

In this embodiment, the expandable layer 18 comprises a layer of hydrogel of the type discussed above embedded with a plurality of activating elements 20. Alternatively, the plurality of activating elements 20 can be disposed between the expandable layer 18 and the inner face 17a of the outer shell 17. In the above embodiments the activating elements 20 are light emitting diodes (LEDs) with a specific wavelength range appropriate for activating the hydrogel. The activating elements 20 are disposed in an evenly spaced arrangement extending circumferentially around the funnel 5 in a series of circumferentially extending rows. However, it will be understood that the arrangement of the activating elements 20 may be varied as will become apparent hereinafter. The breast pump 1 further includes a control unit (not shown) to operate the activation elements 20. The control unit (not shown) is configured to operate the activation elements 20 so that they are operated individually or in combination with other activation elements 20. Further, the control unit (not shown) is configured so that the activation elements can be operated in a predetermined sequence. The control unit (not shown) is connected to the activating elements 20 by conventional means, for example electrical wires.

An operating button (not shown) is formed on the main body to control operation of the breast pump, as will be described hereinafter. Low power long life cell batteries (not shown) are disposed in the main body to power the control means (not shown) and activating elements 20. In a breast pump comprising a motorized vacuum pump unit, the low power long life cell batteries (not shown) may also be used to power the motorized vacuum pump.

Although the batteries (not shown) are disposed in the main body, it will be understood that alternatively the batteries may be integrally formed with the funnel 5 or mounted to the funnel 5.

The protective membrane 19 extends over an inner face 21 of the expandable layer 18 such that the expandable layer 18 is sandwiched between the protective membrane 19 and the outer shell 17. The protective membrane 19 comprises a main portion 22, an inner portion 23 and an outer portion 24. The inner portion 23 communicates between the protective membrane main portion 22 and a lower end 25 of the outer shell 17 and the outer portion 24 communicates between the protective membrane main portion 22 and an upper end 26 of the outer shell 17. Each of the protective membrane inner and outer portions 23,24 are fixedly disposed against or to the outer shell 17 such that the expandable layer 18 is fully enclosed by the protective membrane 19 and the outer shell 17.

Although in the above embodiment the expandable layer 18 and the protective membrane 19 do not extend into the hollow passage 16 of the cylindrical portion, it will be understood that in another aspect of the invention the expandable layer and the protective membrane may partially extend therein to locate against an inner surface 28 of the hollow passage, to increase the massaging of the nipple of a user disposed in the breast pump during use, as will become apparent hereinafter, and to increase comfort so that the nipple cannot contact the cylindrical portion 7. In this case, activating elements 20 are disposed in the portion of expandable layer disposed in the hollow passage.

The protective membrane 19 is formed from a resilient material such as a rubber or plastic such that it can deform and swell in accordance with the expansion of the expandable layer 18 as will become apparent hereinafter. The pliability of the membrane also acts to increase the comfort of a user.

Operation of a breast pump according to the above embodiment of the present invention will now be described with reference to the Figures.

A user takes the breast pump 1 and positions the conical portion 6 of the funnel 5 such that a portion of the user's breast, including the nipple and areola, is disposed in the hollow recess 9. The upper end 12 is located against the user's breast to form a seal there between such that a negative vacuum may be formed in the hollow recess 9. The resilient nature of the outer portion 24 of the protective membrane 19 and/or the expandable layer 18 aids the sealing of funnel 5 against the user's breast.

A negative pressure is formed in the hollow recess 9 by operating the vacuum pump unit (not shown). In this embodiment, the vacuum pump unit is operated by operating the handle 4. The negative pressure helps to maintain the breast pump 1 in position relative to the breast even when no support is provided externally. Additionally, the negative pressure helps to induce milk extraction from the user's breast.

When a negative pressure is applied, the nipple is extruded into the hollow recess 9 such that a substantial portion of the surface of the nipple, areola and breast disposed in the hollow recess 9 is in contact with the inner surface 10 of the hollow recess 9 which is defined by the protective membrane 19. The breast pump is then maintained by the user at a vacuum of desired pressure, such that it is locked in a position of optimum comfort for said user.

Next, the hydrogel of the expandable layer 18 is activated by the activation elements 20. The user presses the operating button (not shown) on the main body 2 to operate the control unit (not shown) in a predetermined mode. The control unit (not shown) operates the activation elements 20 such that they emit heat or light energy at a specific wavelength range dependent on the hydrogel of the expandable layer 18 such that the hydrogel of the expandable layer 18 is activated. When an activation element 20 is operated, the hydrogel surrounding said activation element 20 expands to cause swelling in proximity to the user's breast. Expansion of the expandable layer 18 in the direction of the outer shell 17 is restricted by the stiffness of the outer shell 17 and so the inner surface 10 is caused to swell into the hollow recess 9 of the funnel 5. The protective membrane 19 is resilient to allow the expandable layer 18 to expand such that the inner surface of the hollow recess 9 swells.

The swelling of the inner surface 10 causes a positive pressure to be applied to the user's breast in contact with the inner surface 10 of the hollow recess 9 and so milk extraction from the user's breast is induced.

The inner surface 10 of the hollow recess 9 therefore swells to fully conform to the breast and nipple of the user, regardless of size and contour.

The control unit activates each individual activation element 20 or a group of activation elements 20 in a predetermined sequence. The sequence by which the control unit operates each activation element 20 or group of activation elements 20 is changed by the user operating the operating button (not shown) between a number of predetermined sequences. The speed of the sequence, and the amount of applied positive pressure on the user's breast, can be controlled by the amount of activation of the hydrogel of the expandable layer 18.

Figure 5:
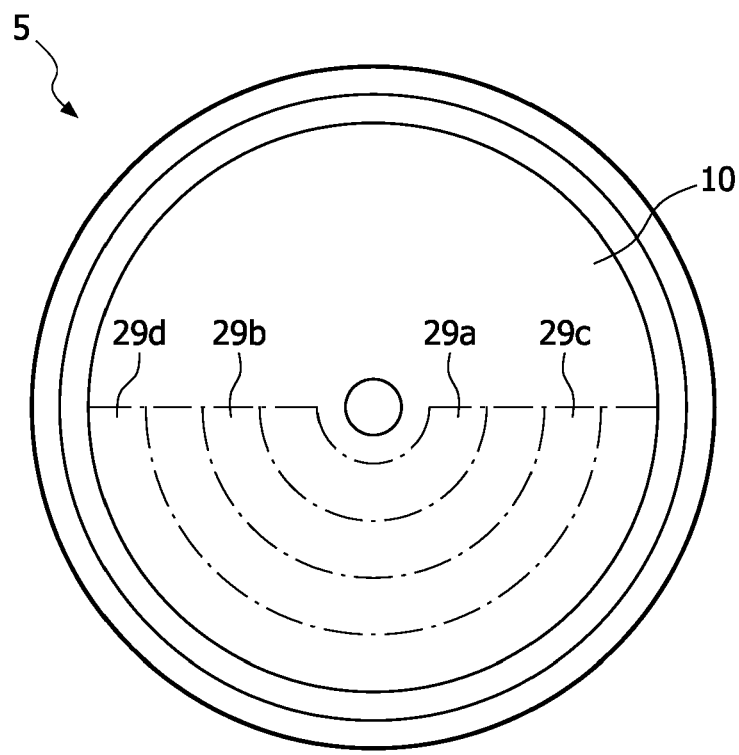
FIG. 5 illustrates a front view of a breast receiving funnel of the breast pump as shown in FIG. 1 showing activating element regions according to one aspect of the present invention.

For example, in one sequence the control unit (not shown) is configured to perform a predetermined sequence of operating the activation elements 20 such that positive pressure is applied to the breast tissue in a peristaltic movement. In one aspect, the control unit (not shown) operates a number of semi-circular groups of activation elements 20, each group arcuately arranged at a different radial distance from the lower end 11 of the funnel 5. Therefore, as each group of activation elements 20 is operated, then different arcuate regions of the expandable layer 18 are activated and the respective region 29a, 29b, 29c, 29d (refer to FIG. 5) of the inner surface 10 swells in sequence dependent on the control unit operating the activating elements 20. If the groups of activation elements described above are operated in a sequence from an upper end 8 to a lower end 11 of the funnel 5, then the respective regions 29a, 29b, 29c, 29d of the inner surface 10 swell in an inwardly orientated sequence.

In the above sequence, wherein only semi-circular groups of activation elements 20 are operated, the other portion of the expandable layer 18 is not activated or is activated by the activation elements 18 disposed therein at a constant rate, such that a constant pressure is applied by said portion. The above sequence is analogous to the action of a suckling baby since it is only the lower jaw and tongue of the infant that move against the nipple and aerola that are clamped against the non-moving top jaw.

Figure 6:
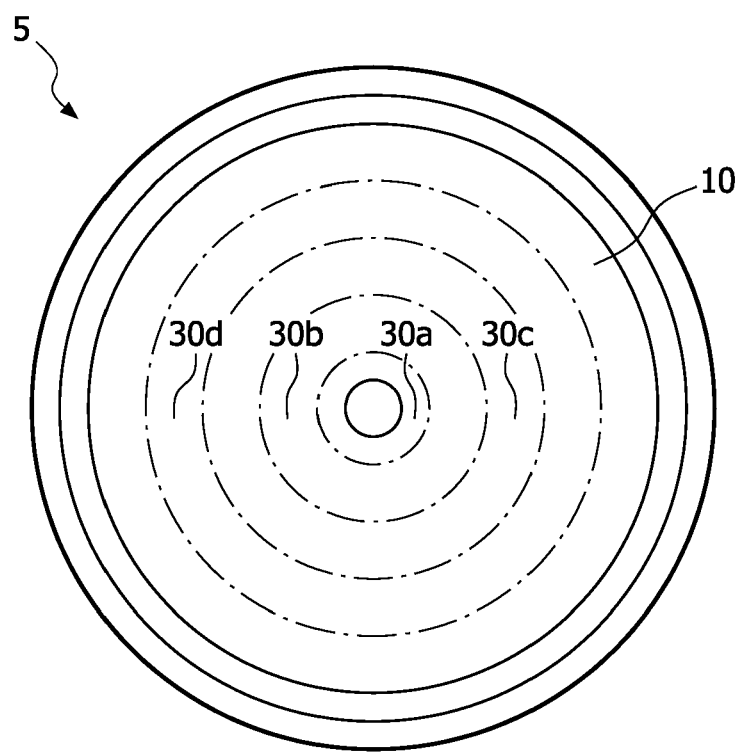
FIG. 6 illustrates a front view of a breast receiving funnel of the breast pump as shown in FIG. 1 showing activating element regions according to another aspect of the present invention.

In another aspect, groups of activation elements 20 circumferentially extending around the funnel 5, at a different radial distance from the lower end 11 of the funnel 5, are operated in sequence such that different arcuate regions of the expandable layer 18 are activated and the respective region 30a, 30b, 30c, 30d (refer to FIG. 6) of the inner surface 10 swells in sequence dependent on the control unit operating the activating elements 20. This arrangement can increase speed and aid efficient expressing of milk from the user's breast.

An advantage of the above embodiment is that it is possible to address engorgement knots in the breast. By using the above embodiment all regions of the breast can be stimulated, as required, to relieve engorgement by the application of positive pressure on the breast due to the swelling of the inner surface 10 of the hollow recess 11.

When a LED is used which emits visible light is used, the outer shell 17 and the expandable layer 18 are transparent such that the operation of the activating elements 20 is visible. This gives a visible indication of the stimulation points of the breast.

Figure 3:
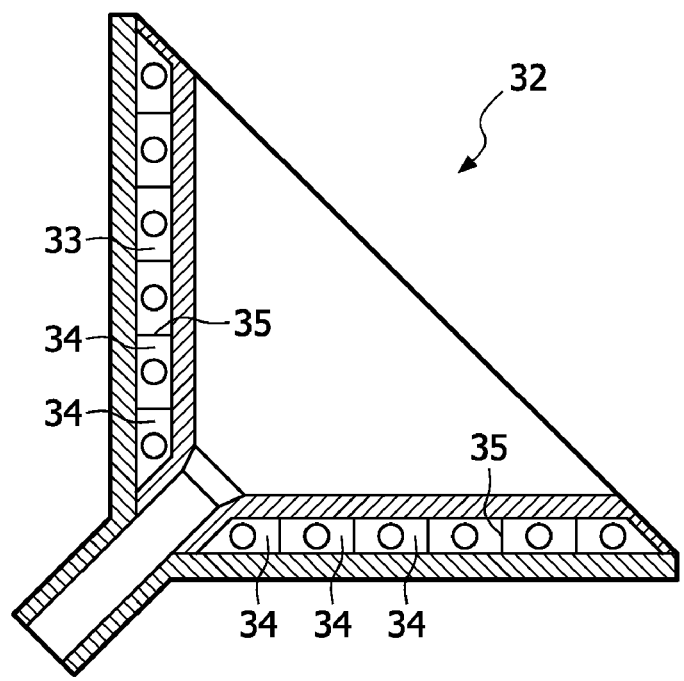
FIG. 3 illustrates another cross sectional view of a breast receiving funnel of the breast pump as shown in FIG. 1 according to a second embodiment of the present invention.

A second embodiment of the invention will now be described with reference to FIG. 3. The breast pump is generally the same as the breast pump 1 described above and so a detailed description will be omitted herein. Features of the breast pump that are generally the same as discussed above retain the same reference numerals.

In this second embodiment the funnel 32 comprises an expandable layer 33 comprising a plurality of discrete cells 34. Each cell 34 is independent from each adjacent cell 34 such that the activation of one cell 34 does not impact the activation of an adjacent cell 34. Therefore, a zone of the inner surface associated with each discrete cell swells independently of an adjacent zone. An insulation layer 35 is formed between each cell 34 to prevent the activating element 20 of one cell 34 from activating an adjacent cell 34, such that the zone of the inner surface of the adjacent cell 34 does not swell.

Although in this embodiment a single activation element 20 is associated with each cell 34, it will be appreciated that the invention is not limited thereto and that more than one activation element 20 may be associated with each cell 34 and the size of each cell 34 may vary. For example, each cell 34 may extend circumferentially around the funnel 5.

Figure 4:
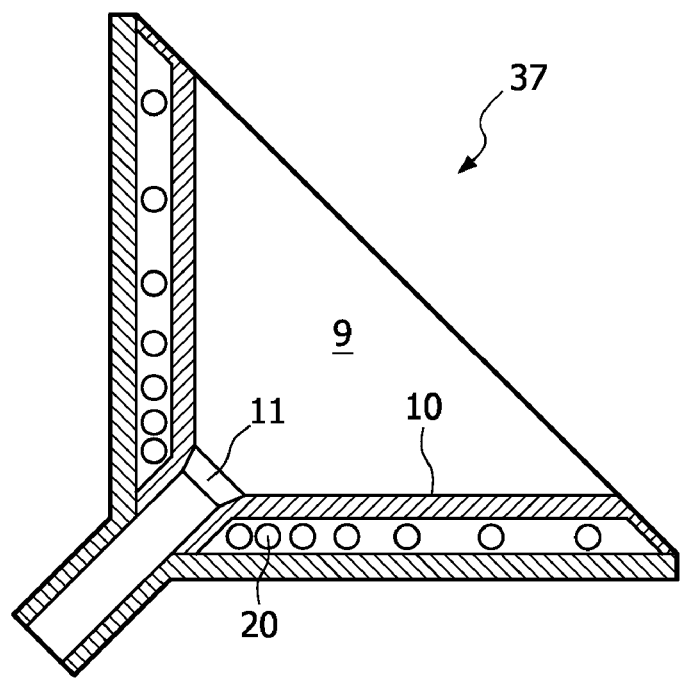
FIG. 4 illustrates another cross sectional view of a breast receiving funnel of the breast pump as shown in FIG. 1 according to a third embodiment of the present invention.

A third embodiment of the invention will now be described with reference to FIG. 4. The breast pump is generally the same as the breast pump 1 described above and so a detailed description will be omitted herein. Features of the breast pump that are generally the same as discussed above retain the same reference numerals.

In the above description the activating elements 20 are disposed in an equally spaced arrangement in the expandable layer 18. However, in this third embodiment the spacing of the activating elements 20 relative to each other becomes denser towards the lower end 11 of the funnel 37, such that a greater number of activating elements 20 are disposed proximate to the lower end of the funnel 37. Therefore, expansion of the expandable layer 18 and hence swelling of the inner surface 10 of the hollow recess 9 can be more tightly controlled and ability to massage the nipple and areola of a user's breast relative to the lower end 11 of the inner surface 10 is increased.

Although in the above third embodiment the expandable layer is not shown divided into a number of discrete cells, it will be understood that the features of the third embodiment of the invention may be used in combination with those features of the second embodiment of the invention.

An advantage of the present invention is that the present invention aids the expression of breast milk from a breast of a lactating female in a way that is more analogous to that of a suckling infant, whilst also providing greater comfort and ease of use.

In each of the above embodiments of the present invention, the expandable layer forms part of the funnel. However, in an alternative embodiment the invention is in the form of a conical insert which is disposable in the funnel. The insert includes an expandable layer which is generally the same as the expandable layer discussed above, and is formed from a hydrogel. The outer surface of the insert is formed to locate in a breast receiving recess of a conventional breast pump funnel and the inner surface is formed to contact a user's breast disposed therein.

The insert also comprises a rigid shell extending around the outside of the funnel, which maintains the shape of the insert and protects it from damage. Activating elements are arranged to activate the expandable layer and a protective layer extends around the inner surface of the expandable layer as described above for the earlier embodiments of the invention.

The insert comprises a lip which is arranged to extend over an outer open end of a conventional breast pump trumpet. An advantage of this arrangement is that wires extending from the insert can extend from an outer edge of the lip outside the conventional breast pump trumpet to connect to an external power source to operate the activating elements and so will not break the pressurized seal of the funnel.

Although in each of the above embodiments, the expandable layer 18 expands from a contracted neutral state when the activating elements 20 are operated, it will be understood that a hydrogel can be used which contracts in response to a stimulation, such as heat or an electrical current. With such an expandable layer 18, the expandable layer 18 is in a neutral expanded state when the activating elements 20 are inoperable and subsequently contracts when the activating elements are operated.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast receiving funnel for a breast pump comprising an expandable layer formed from a hydrogel which is configured to undergo a volumetric expansion such that an inner surface of the breast receiving funnel, against which a user's breast is locatable, swells towards said user's breast to apply a positive pressure thereto and aid the expression of milk therefrom.

2. A breast receiving funnel for a breast pump according to claim 1, further comprising an activating element which is operable to cause the expandable layer to expand or contract.

3. A breast receiving funnel for a breast pump according to claim 2, wherein the expandable layer comprises a plurality of discrete cells of hydrogel which are independently activatable such that a zone of the inner surface associated with each discrete cell is configured to swell independently to an adjacent zone.

4. A breast receiving funnel for a breast pump according to claim 2, further comprising a plurality of activating elements.

5. A breast receiving funnel for a breast pump according to claim 2, wherein the activating element is disposed in the expandable layer.

6. A breast receiving funnel for a breast pump according to claim 5 wherein the activating element is operable to emit heat and/or light energy and the expandable layer is activated by said heat and/or light energy such that it expands or contracts.

7. A breast receiving funnel for a breast pump according to claim 1, wherein a protective membrane is disposed on a surface of the expandable layer and the protective membrane forms the inner surface of the breast receiving funnel.

8. A breast receiving funnel for a breast pump according to claim 7, wherein the breast-receiving funnel further comprises a rigid shell and the expandable layer is disposed between the rigid shell and the protective membrane.

9. A breast receiving funnel for a breast pump according to claim 8 wherein the protective membrane seals to said rigid shell such that the expandable layer is enclosed therein.

10. A breast receiving funnel for a breast pump according to claim 8, further comprising a control unit configured to operate a plurality of activating elements in a sequential manner such that zones of the inner surface, which are associated with each activating element, swell periodically in a predetermined sequence causing the zones of the inner surface to move inwardly and outwardly relative to the user's breast and apply a peristaltic pressure thereto.

11. A breast pump comprising a breast-receiving funnel according to claim 1.

12. An insert adapted to fit on a breast-receiving funnel of a breast pump comprising an expandable layer formed from a hydrogel which is configured to undergo a volumetric expansion such that an inner surface of the insert, against which a user's breast is locatable, swells towards said user's breast aid the expression of milk therefrom.

13. An insert according to claim 12, wherein a protective membrane is disposed on a surface of the expandable layer and the protective membrane forms the inner surface of the insert.

14. An insert according to claim 13, wherein the protective membrane encloses the expandable layer such that the expandable layer is sealed therein.

15. An insert according to claim 14 wherein the protective membrane seals to a rigid shell such that the expandable layer is enclosed therein.

* * * * *